United States Patent
Green et al.

(10) Patent No.: US 9,131,943 B2
(45) Date of Patent: Sep. 15, 2015

(54) NON-PNEUMATIC TOURNIQUET DEVICE

(75) Inventors: William J. Green, San Clemente, CA (US); Ted J. Brackett, Manhattan Beach, CA (US)

(73) Assignee: PRECISION MEDICAL DEVICES, LLC, Thousand Oaks, CA (US)

( * ) Notice: Subject to any disclaimer, the term of this patent is extended or adjusted under 35 U.S.C. 154(b) by 1013 days.

(21) Appl. No.: 12/897,770

(22) Filed: Oct. 4, 2010

(65) Prior Publication Data

US 2011/0022077 A1 Jan. 27, 2011

Related U.S. Application Data

(63) Continuation of application No. 29/346,791, filed on Nov. 5, 2009, now Pat. No. Des. 642,275, and a continuation-in-part of application No. 12/114,737, filed on May 2, 2008, and a continuation-in-part of application No. PCT/US2008/062583, filed on May 2, 2008.

(60) Provisional application No. 61/278,315, filed on Oct. 4, 2009, provisional application No. 60/915,665, filed on May 2, 2007, provisional application No. 61/046,404, filed on Apr. 18, 2008.

(51) Int. Cl.
*A61B 17/00* (2006.01)
*A61B 17/132* (2006.01)
*A61B 19/00* (2006.01)

(52) U.S. Cl.
CPC ..... *A61B 17/132* (2013.01); *A61B 2017/00438* (2013.01); *A61B 2019/307* (2013.01)

(58) Field of Classification Search
CPC ............. A61B 17/132; A61B 17/1322; A61B 17/1325; A61B 2017/00438; A61B 2017/00442; A61B 2019/307
USPC .............. 606/203, 201, 204, 151; 600/39, 41, 600/208; 128/842, 843
See application file for complete search history.

(56) References Cited

U.S. PATENT DOCUMENTS

| | | |
|---|---|---|
| 2,333,237 A | 11/1943 | Erekson |
| 3,675,657 A | 7/1972 | Gauthier |
| 3,705,580 A | 12/1972 | Gauthier |
| 4,173,978 A | 11/1979 | Brown |
| 4,228,792 A | 10/1980 | Rhys-Davies |
| 5,181,522 A | 1/1993 | McEwen |
| 5,304,188 A | 4/1994 | Marogil |

(Continued)

OTHER PUBLICATIONS

Printout from http://www.marmedco.com for the TOURNI-COT product (1 page).

(Continued)

*Primary Examiner* — Katherine Rodjom
(74) *Attorney, Agent, or Firm* — Law Office of David Hong

(57) ABSTRACT

This invention presents a non-pneumatic tourniquet device designed for quick, easy application to an injured digit, such as a finger or a toe. One preferred embodiment comprises an frame, which is affixed to a flexible layer or membrane, and allows for an opening for the insertion of the injured digit through the device. This easy to use apparatus temporarily checks the bleeding or blood flow by applying an external pressure or a compression to the blood vessels in an appendage and also allows for exsanguination of the injured area.

12 Claims, 6 Drawing Sheets

(56) References Cited

U.S. PATENT DOCUMENTS

| | | |
|---|---|---|
| 5,304,202 A | 4/1994 | Stahl |
| 5,607,448 A | 3/1997 | Stahl |
| 5,628,329 A | 5/1997 | Bennett |
| 5,997,469 A | 12/1999 | Northcutt |
| 6,319,194 B1 | 11/2001 | Wulf |
| 6,569,083 B1 | 5/2003 | Kassman |
| 6,843,253 B2 | 1/2005 | Parkes |
| 6,916,289 B2 * | 7/2005 | Schnall .................. 600/500 |
| 2003/0009087 A1 | 1/2003 | Keirsbilck |
| 2007/0073335 A1 | 3/2007 | Carter-Smith |

OTHER PUBLICATIONS

U.S. Appl. No. 61/693,244, filed Aug. 24, 2012; Inventor: Green and Brackett.

U.S. Appl. No. 62/000,508, filed May 19, 2014; Inventor: Green and Brackett.

* cited by examiner

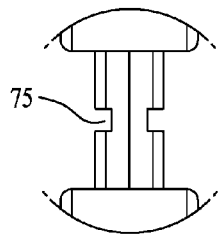
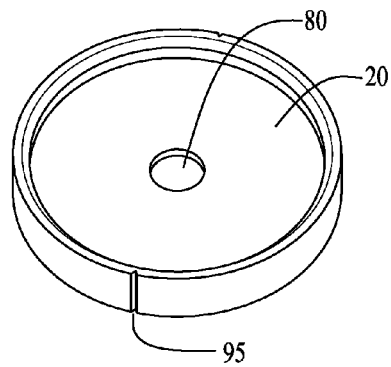
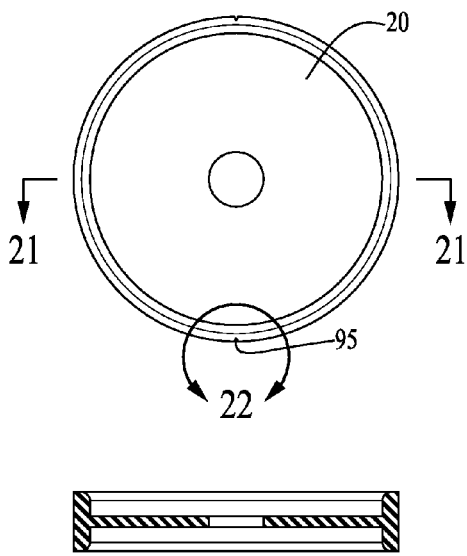
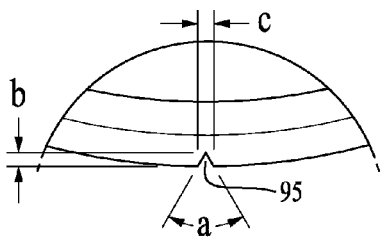

NON-PNEUMATIC TOURNIQUET DEVICE

This application claims priority to U.S. Provisional Patent Application Ser. No. 61/278,315, filed on Oct. 4, 2009. This application is a continuation of U.S. Design application 29/346,791, filed on Nov. 5, 2009 now U.S. Pat. No. D642,275.

This application is also a continuation in part of U.S. Utility patent application Ser. No. 12/114,737, filed on May 2, 2008 and PCT/US08/62583, filed on May 2, 2008, which both claim priority to U.S. Provisional Patent Application Ser. No. 60/915,665, filed on May 2, 2007 and Ser. No. 61/046,404, filed on Apr. 18, 2008; these applications are incorporated by reference. Also, this application is related to U.S. Design application 29/317,784, filed on May 6, 2008.

BACKGROUND OF THE INVENTION

1. Field of the Invention

This invention relates to a non-pneumatic tourniquet and medical device designed for quick, easy application to an injured digit (finger or toe). There is an apparatus for (1) temporarily checking the bleeding or blood flow by applying an external pressure or a compression to the blood vessels in an appendage (finger, toe, etc.) and for (2) providing exsanguination of the appendage and for (3) providing multiple ways for removing said apparatus without disturbing the surgically repaired area.

2. Description of Related Art

There have been numerous articles written over the past several years by plastic surgeons, orthopedic surgeons, dermatologists, emergency physicians, podiatrists and hand specialists detailing the requirements of an effective digital tourniquet. There have been many methods proposed, but there are none without some inherent deficiency or inefficiency.

The general consensus for the necessary requirements include ease of application and removal, universal use, comfort, easily seen (not likely to be left in place leading to digital necrosis), and most importantly, the ability to provide a bloodless environment with maximal visualization of the necessary structures.

It has been demonstrated that to achieve a truly bloodless field, free from "oozing" into the wound of venous blood trapped in the digit when the tourniquet is applied; one needs to exsanguinate the digit prior to application of the tourniquet. The methods that do not first exsanguinate the digit or appendage commonly experience this problematic persistent oozing, and may include the Penrose drain and pneumatic tourniquets.

The techniques that do exsanguinate the digit first include the "cut glove" technique and the Marmed Tourni-quot device. Each of these techniques do not compare to utility of the "T-Ring" device when considering ease of application, universality of use, and safety and ease of removal. The "cut glove" and the Tourni-quot product are similar to a rubber ring or donut, but this rubber ring style product has many inherent advantages. One major disadvantage is when the rubber ring is applied to an injured digit, the user must roll the ring up the digit and over and through the injured area. During this process, the rubber ring device not only may increase the damage to the injured area, but also may catch any traumatic skin flaps or lacerations. This rubber ring structure does not allow for increasing the diameter of the rubber ring apparatus.

In addition, it is recommended that all current devices that are rolled onto the finger need to be cut off, which requires additional sterile instruments and have the potential to injure the digit during the removal process. From the preceding descriptions, it is apparent that the devices currently being used have significant disadvantages. Thus, important aspects of the technology used in the field of invention remain amenable to useful refinement.

SUMMARY OF THE INVENTION

The present invention or "T-Ring" device has several advantages over current devices used as tourniquets for finger and toe procedures. The disclosed invention has both unique methods of application, which allows for exsanguination (the action or process of draining or losing blood); applying tourniquet pressure to a digit (including without limitation: appendage, finger, leg or arm); and multiple ways for easy removal of the apparatus. This unique method of application and removal provide additional utility, safety and ease of use as compared to current devices available to health care providers.

The "T-Ring" device has been designed to meet all of the requirements of the "ideal" digital tourniquet. Many devices have been used in emergency departments and in the operating suites, and the applicant believes that none provides the effectiveness, safety and efficiency demonstrated by the applicant's "T-Ring" device.

An apparatus for improving an operating field on an appendage or digit of a patient comprising: a preferably rigid or firm frame, which has a flexible layer or membrane and a membrane opening. The frame has a frame surface, a peripheral edge, a first end, a second end, and a centrally disposed opening. The frame can further have at least one groove or break point, which is oriented in between the first and the second end. The at least one groove or break point is at a lower elevation than the top surface of the frame, and the user is able to stretch apart the device; this break point can form a shelf on the rigid frame.

The frame surface can have at least one aperture along the peripheral edge of the frame; the frame can have a first and a second end; each end can have a tab, which can outwardly extend past the peripheral edge of the frame, and have boss structures or friction nubs. The frame can have at least one groove or notch, which is oriented in between the first and the second end.

The frame can have a flexible membrane having a first membrane portion and a second membrane portion; the first membrane portion can cover the frame, except for the first and the second tabs; the second membrane portion can form a web with a centrally disposed membrane opening; and the web is able to slidably engage an appendage of a patient; the flexible membrane can have at least one hole located approximately near the at least one frame groove.

The apparatus and frame can have various additions, including without limitation: at least one light emitting diode, which is connected to a battery; at least one bladder for holding antiseptic material; the frame surface has at least one frame boss or nub; the flexible membrane has at least one integral support rib.

The present invention introduces such refinements. In its preferred embodiments, the present invention has several aspects or facets that can be used independently, although they are preferably employed together to optimize their benefits. All of the foregoing operational principles and advantages of the present invention will be more fully appreciated upon consideration of the following detailed description, with reference to the appended drawings.

BRIEF DESCRIPTION OF THE DRAWINGS

FIG. 17 is a cross-sectional view of a section of the frame of FIG. 12 and along the sight lines shown in FIG. 16.

FIG. 18 is a close up view of a section (break point or breakable) of the frame of FIG. 12 and along the sight lines shown in FIG. 15.

FIG. 19 is a perspective view of the inner flexible membrane of FIG. 8.

FIG. 20 is a first or top view of the inner flexible membrane of FIG. 19.

FIG. 21 is a cross-sectional view of the inner flexible membrane of FIG. 20.

FIG. 22 is a close up view of one section of the inner flexible membrane of FIG. 20.

Figure 1:
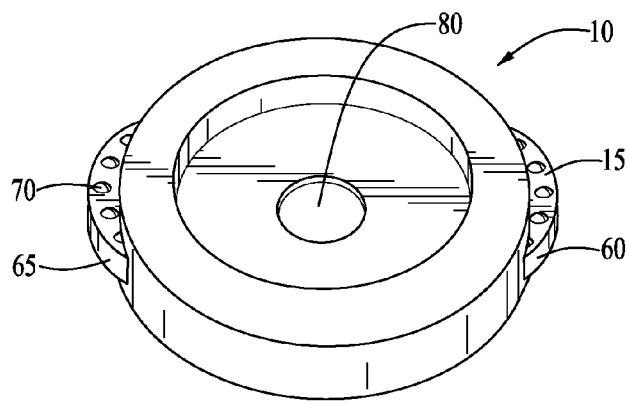
FIG. 1 is a perspective view of one preferred embodiment of the invention.
Figure 2:
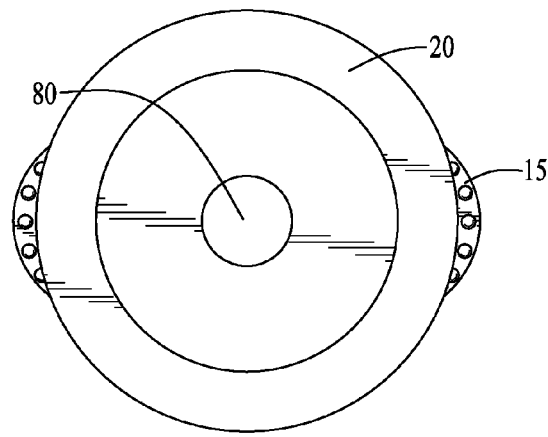
FIG. 2 is a view of a first side of one preferred embodiment of the invention.
Figure 3:
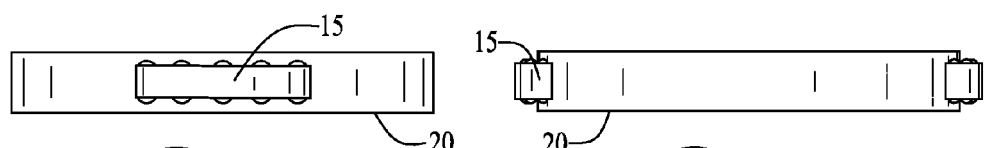
FIG. 3 is a view of a third side of one preferred embodiment of the invention.
Figure 4:
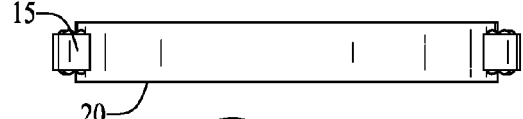
FIG. 4 is a view of a fifth side of one preferred embodiment of the invention.

PARTS LIST 10 apparatus
15 frame
20 membrane or flexible layer
30 peripheral or outer frame edge
35 first end of frame
40 second end of frame
45 opening within frame
50 frame surface
55 openings or grasping points on peripheral edge of frame
60 first tab
65 second tab
70 boss on tab
75 notches or grooves on frame
80 membrane or flexible layer opening
85 cut outs on membrane
90 breakable areas or break points on frame
95 slit or groove on flexible membrane
100 channel formed between the breakable area of the frame and the flexible membrane
105 shelf or bridge on breakable area on frame

DESCRIPTION OF THE PREFERRED EMBODIMENTS

The "T-Ring" device is a non-pneumatic tourniquet device designed for quick, easy application to the involved digit (finger or toe) or other appendage of the patient. There is an apparatus 10 for improving an operating field for medical procedures comprising a substantially rigid frame 15 with a flexible membrane covering 20, which can be a full or partial covering of the frame.

Figure 6:
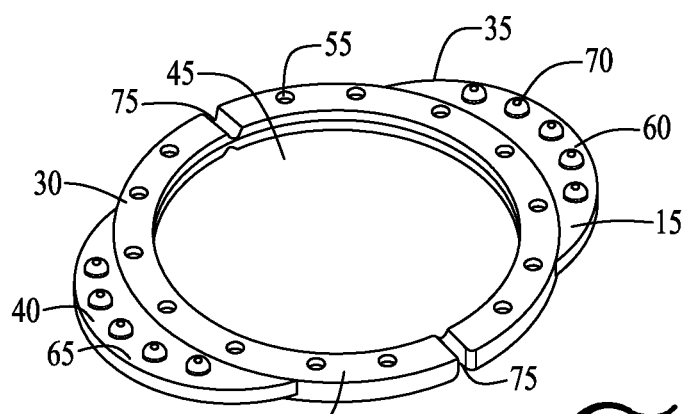
FIG. 6 is a perspective view of the inner frame of one preferred embodiment of the invention.

Frame:

As shown in FIG. 6, the apparatus 10 has a substantially rigid and circular shaped frame 15 with a peripheral outer edge 30 and surface 50. This frame has a first end 35 and a second end 40. This invention allows for other geometric or arbitrary frame shapes.

The frame further has a centrally disposed opening 45. Note that this opening should be large enough to accommodate the digit or body part of the patient and to provide enough room around the digit or body part to allow flexion of the membrane or flexible layer part and for removal of the apparatus.

The frame further has at least one frame surface 50. The frame surface has at least one aperture or opening, which is oriented along the peripheral edge of the frame and passes partially or completely through the frame. FIG. 6 shows multiple openings 55 or grasping points or apertures around the circumference or peripheral edge of the frame. These multiple openings, apertures or grasping points act as anchor sites for parts of the flexible membrane to grasp and to interconnect with the frame. The openings act as female parts for the flexible layer or membrane, which can act as a male part.

FIG. 6 shows the aperture or opening as being parallel to the centrally disposed opening; however, other embodiments may have these openings placed at an angle to the centrally disposed opening or to have internal structures to maximize the gripping or grasping interaction of the flexible membrane to the frame.

Grasping Points or Tabs:

FIGS. 1 to 7 show embodiments with the frame having a first tab 60 and a second tab 65 at the opposite ends of the frame body. Other embodiments may allow for more than two tabs, which are strategically located around the frame body to further assist the physician in removing or utilizing the T-Ring apparatus.

The first and the second tabs can also have at least one boss 70, bump, protrusion or resistance and grasping structure on the tab surface. These resistance points on the surface of the tab help the user grasp the apparatus. These tabs outwardly extend past the peripheral edge of the frame. The tabs may also be grooved or a convex shape to readily accept a user's finger.

Figure 7:
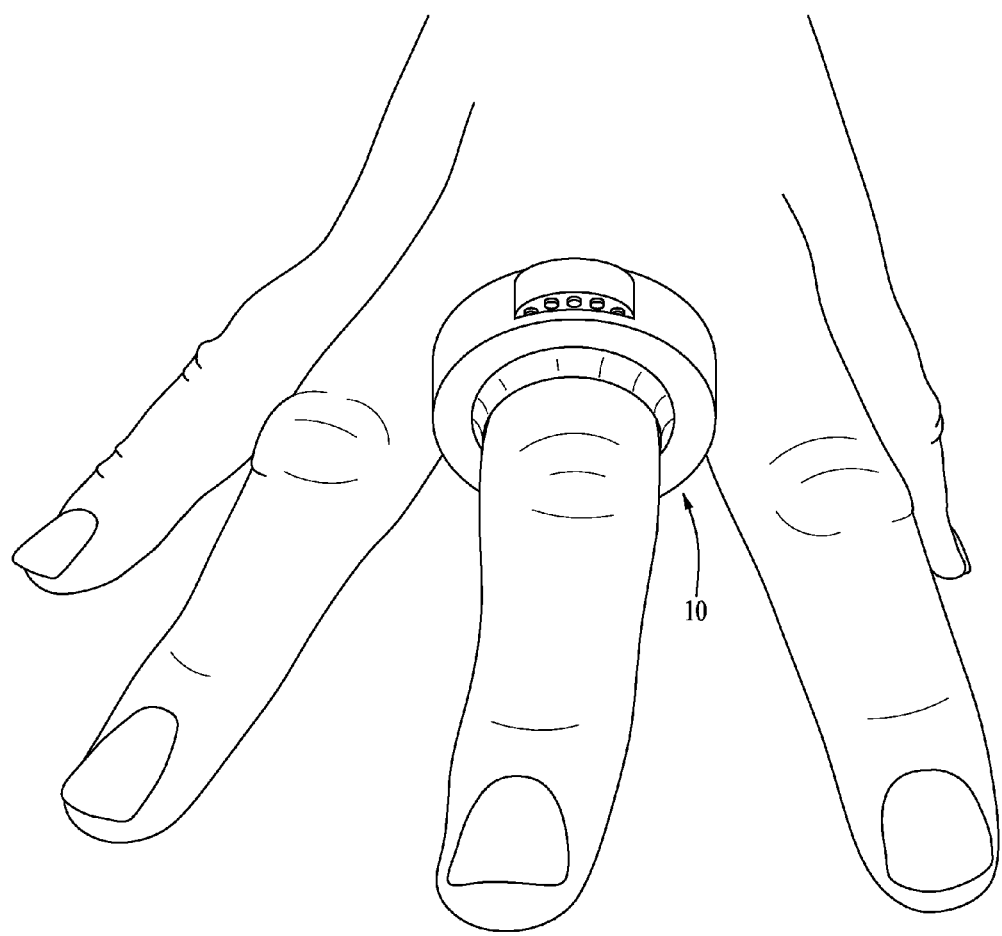
FIG. 7 shows the apparatus engaging a human finger; note how the flexible layer or membrane effectively grasps the digit.

Break Points or Grooves:

The frame can also have at least one break point 75, scoring, groove or indentation, which is oriented in between the first and the second end. FIG. 7 shows two break points or scores, which are located between the first and the second end; each break point is oppositely opposed to one another. This at least one break point allows the user to easily snap the frame (from a first unsnapped position to a second snapped position) so that the user can expand the apparatus further beyond the non-snapped frame diameter, especially over any repaired area of the patient's finger or digit. These break points are not critical to the basic function of this device (i.e., exsanguination), but these break point structures do provide an additional level of function not disclosed by the prior art.

Flexible Layer or Membrane:

As shown in FIGS. 1 to 5, there is a flexible layer or membrane 20, which covers the frame and substantially covers the frame opening. This flexible layer or membrane has a membrane opening 80, which is centrally located in the device. The material used for the flexible membrane can be thermoplastic elastomer (TPE) or other types of rubbers, plastics or flexible materials. This flexible layer can completely or partially cover the inner frame and/or tabs.

As shown in FIG. 1, the outermost area of flexible layer or membrane grabs and conforms to the shape of the inner frame; FIG. 1 version shows that the tabs are not covered by the membrane. This membrane has a first or outer portion and a second or inner portion. Looking at the device from the side, the first or outer portion is a higher elevation than the second or inner portion.

As one leaves the first or outer portion of the membrane, the second or inner portion of flexible layer or membrane is no longer conforming to the shape of an internal structure and becomes a web. This second or inner membrane portion can be described as a means located within the inner frame of the device for grasping or grabbing the patient's finger, digit or appendage.

In FIG. 1, this web or inner portion of the flexible layer or membrane lacks any internal structures, ribs or components. It is preferred that the terminal end or edge of the web or inner portion of the membrane be flexible enough or take advantage of the flexible nature of the membrane to best grasp or grab the patient's digit or appendage during use. Different flexible materials (with different durometer) can be used to customize the efficiency of the device for the particular use. However, as noted below, other possible embodiments allow for the addition of blade or gripping structures on the inner surface of the membrane opening 80.

In addition, this membrane can also pass through the at least one aperture/openings through the frame; and the web also has a centrally disposed membrane opening 80. This membrane opening should be parallel with the frame opening.

The size of the membrane opening 80 should be large enough to accommodate the patient's digit or body part and to provide resistance in order to effectively provide pressure to the digit as the apparatus is slid into place or for effective exsanguination of the body part or digit. In FIG. 7, the inner part of the flexible layer or membrane grabs and grips the finger and applies an external pressure or a compression to the blood vessels in the patient's appendage.

Manufacturing Process for One Preferred Embodiment:

For one preferred embodiment, the process to manufacture the preferred embodiment is to injection mold a single frame piece (including without limitation a hard plastic outer ring). Then, the single frame piece is "over-molded" with the flexible material (including without limitation thermoplastic elastomer or TPE); the frame is encapsulated except the two tabs. Other embodiments allow for multiple frame pieces, but for cost savings, it is preferable to injection mold a single frame piece.

The outer ring frame can have at least one or preferably an array of holes or apertures that pass partially or completely through the frame body to help anchor the flexible material to the frame and to provide the taught "trampoline" effect of the flexible layer or membrane. Other embodiments allow the holes or apertures to have additional internal structures such as footings to further improve the gripping effect of the flexible material within the frame.

A most basic version of this invention can also employ a flexible but at the same time firm plastic or rubber-style ring. This type of ring would not require a separate internal frame. In another possible embodiment, the invention or the "T-Ring" device can also comprise a central thin, flexible rubber disc surrounded by a hardened outer plastic ring. The outer ring is made of two identical halves which, when sealed together (heat stamped or glued, for example), enclose and anchor the central rubber or plastic disc.

The central rubber disc is made with a "hole" in its center, which allows the "T-Ring" apparatus to be placed over a finger or toe. This hole or opening is smaller than the diameter of the involved digit, so that pressure will be applied to the digit as the ring is slid into place. Other embodiments envision the outer ring to be a single piece unit that houses or contains or holds the center rubber disc.

How the Apparatus Works:

The health care provider will grip the "T-Ring" device or apparatus by its outer hardened ring or frame and slide the apparatus up the appendage, finger or toe to its base on the hand or foot. The outer ring "drags" the inner section or membrane with it, effectively exsanguinating the digit as the "T-Ring" apparatus is placed on the digit. See FIG. 7.

Since the central rubber disc or membrane is flexible and is suspended from the outer ring and lags behind it during application, the inner hole is effectively pulled up and over any protrusions on the digit. This central flexible disc structure or membrane further allows the "T-Ring" device to slide over lacerations, avulsions and, more importantly, traumatic skin flaps. Once in place, the "T-Ring" device or apparatus applies enough pressure to maintain hemostasis, and thus, this invention provides a bloodless operating field.

The "T-Ring" device allows for differing sizes or diameters of the central rubber hole or opening. There is a standard sized hole or opening, which will be utilized on the majority of patients. There will also be versions of the invention with smaller central holes or openings in the cases that increased pressure is necessary to achieve hemostasis, and rings with larger holes in the case where there may be an unusually large flap or irregularity that must be accommodated by the "T-Ring". Note that this invention capitalizes on the difference in flexibility and resistance between the outer ring and the inner flexible ring.

Specifications:

In one preferred embodiment, the outer plastic ring can have an approximate outer diameter of 3.5 cm and inner diameter of 2.5 to 3.0 cm; there will be varying sizes, smaller for pediatric patients and larger for patients with larger digits.

The outer ring can be approximately 0.5 to 1.0 cm in width and 0.5 to 1.0 cm in thickness; note that thickness includes the two plastic "halves" and the central rubber disc (as noted in some versions in the provisional application). This preferred size range provides ease of handling for the health care provider, nicely separates the digits to maximize visualization and the functional work area, and provides a comfortable fit for the patient. These measurements and dimensions are for example only and are not intended to be limiting.

Scoring or Notches on the Outer Ring Structure:

The outer ring can be scored at the 3 o'clock and 9 o'clock positions or orientations (with reference to the numbers on a clock); these scoring or notches allow the outer ring to be easily "snapped" in two pieces when the procedure is completed. To break the apparatus at the score points, the user holds ring in the 12 o'clock and 6 o'clock positions and flexes the ring forwards or backwards until the outer ring frame has snapped.

Once the outer ring has been "snapped," the central hole may be enlarged by pulling on the opposing halves of the outer ring. This will allow the "T-Ring" device to be removed from the digit without the rubber material from the central disc coming into contact with the repaired portion of the digit; this structure allows for a safe and efficient removal. This invention allows for the ring apparatus to be easily removed from the finger in the same fashion that it was placed on the finger; this "snap" option provides an additional margin of safety with more complex injuries or procedures. Other embodiments allow for the outer ring to have grasp or hold points or tabs so that the user may more easily grab the apparatus at positions approximately ninety degrees from the score or notches in the outer ring.

Other Possible Embodiments

1. T BAND Embodiment.

Another embodiment of the invention employs two separate portions or tabs that are interconnected with a flexible membrane with a centrally disposed opening. Unlike the previous embodiments with uniformly closed frame or ring, other embodiments employ completely separate tabs or portions. There will not be break points since the first and the second pieces of the frame are already separate. There can be at least two pieces, but other embodiments allow for three or four pieces, which are all connected to a centrally disposed flexible membrane with an opening for the digit or body part.

2. Two Part Outer Ring.

Other embodiments may employ a first half and a second half of the outer ring. These two halves of the outer ring can be connected via a spring or other elastic cord or rope so to enable the user to take the apparatus from a closed or first position to a second or extended position. The connecting spring or elastic cord or rope between the outer ring halves enable the user to move from the first position to the second position and back to the first position.

3. "O-Ring" Version.

In another embodiment, regarding the outer ring, the first and second rings can mirror one another in shape and dimension. The first and outer rings have a first or outer circumference and a second or inner circumference. There are score marks or indentations placed on opposite sides of the ring; these score points or notches enable the user to separate first and second rings separately into two relatively similar sized halves when the apparatus is stretched open and being removed from a finger or digit. The first and second rings can be made from O-Rings or other commonly used circular washers or rings. The material can be plastic, paper or a composite material.

The middle or third layer of the apparatus is composed of a flexible material, including but not limited to rubber, plastic, or latex; there is an opening in the center of this third layer to allow a finger or toe to enter and to pass through this apparatus. This material should be flexible enough to allow placement of the apparatus around an appendage (finger or toe), but it should be strong enough to maintain pressure at a specific location and to allow for exsanguination of the appendage.

Construction of the apparatus involves sandwiching the third layer of a flexible plastic material or web between two similarly shaped first and second layers (such as O-rings). An opening or hole is placed in the middle of the third layer, and score points or notches are placed at the opposite ends of the apparatus on both the first and second layers.

4. Raised Ridges in Flexible Membrane.

Other embodiments employ raised rubber ridges, which can be molded in a rifle or other types of patterns. These ridges can help the user to screw or to rotate said apparatus on the patient's body part or digit. Other versions can have a thickening rib or support vertebra in the inner flexible membrane to provide more stability during use.

5. Lighting.

Other embodiments may allow for at least one or multiple small light emitting diode (LED) lights to be placed on the peripheral edge of the frame or the tabs. The tabs can also hold a small battery, which are connected to the LED lights.

6. Additional Grasping Points or Bosses on the Inner Surface of the Frame:

Other embodiments can have boss structures or grasping points on the inner surface of the frame to help the flexible membrane to grasp and to interconnect with the frame. Other embodiments can have a lip or a shelf structure or groove, which is molded down the center of the inner surface of the frame, to allow the flexible membrane to more firmly interact and to affix.

7. Inner Blades or Gripping Points on the Inner Surface of the Flexible Membrane.

Other embodiments can have "blades" or gripping points on the inner surface of the flexible membrane opening to better grip and "squeegee" fluid or exsanguinate the patient's digit or body part.

8. Bladders of Antiseptic or Disinfectant or Other Medical Substances in Apparatus:

Other embodiments can have plastic bladders of topical antiseptic or disinfectant, which are located in the frame tabs or even the flexible membrane areas and are sent through tiny holes in the ends of the bladder and are applied to the patient's digit or body part while sliding over. These bladders can be placed in the tabs, and by squeezing the tabs and breaking the bladders, the contents can be released.

9. Cone Shaped Flexible Membrane:

Other embodiments can have cone shaped flexible membrane, which are concave shaped to exaggerate the clinging effect of the apparatus on the digit. The concave shape of the molded flexible material/web can more easily accept the wounded digit.

10. Customizing the Durometer of the Flexible Membrane for the Particular Use.

Other embodiments may alter the flexibility and the tension characteristics of the flexible membrane material to customize the apparatus for a particular kind of purpose, digit or body part. Also, this apparatus can be specifically customized for particular types of tissues or nerves by altering the tension and thickness of the flexible membrane material and also the hole/opening size.

11. Holes Added to the Outer Elastic Layer.

Figure 5:
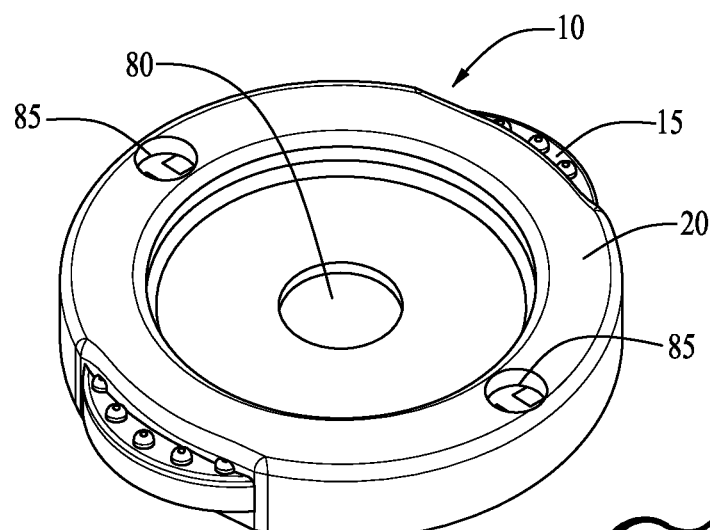
FIG. 5 is a perspective view of another preferred embodiment with cut out sections of the outer flexible or membrane layer. These cut out portions can be on both sides or on one side of the device.

As shown in FIG. 5, at least one hole 85 is added to the elastic material layer, which covers the inner frame, in order to reduce the material thickness in front of each of the score points; this at least one hole should be placed both on the front and the rear side of the apparatus. In one preferred embodiment, there are two score points (3 and 9 o'clock positions) on each side; as a result, there will be a total of 4 holes in this outer elastic material layer. These holes will add in the rings elasticity during the removal process. Note that the holes do not need to completely extend to the surface of the inner frame. Other embodiments will extend all the way to the inner frame.

12. Two-Piece Inner Frame with an Outer Elastic Layer.

Another possible embodiment employs using a two-piece inner frame with a flexible outer layer. Instead of using a single internal frame with score points at the 3 and 9 o'clock positions; the inner ring structure would be split or made into two relatively evenly proportioned pieces. These two parts can form an oval shape. Other frame shapes such as square or rectangular or oval can be employed.

The parts A and B can be joined using a male/female connection apparatus at the meeting junction of the two parts. The meeting section allows one half of the frame to be hollowed out (female half), while the other half (male half) would have a portion that is smaller than the rest of the frame and would insert inside or engage the female part. These parts A and B would be molded separately and inserted together during manufacturing. This two piece unit allows a first (closed position) and a second (open position).

Once together, the elastic TPE material would be integrated over the two piece frame in a fashion similar to the earlier T-Ring prototype. The over-molded TPE material would effectively hold the two halves A and B together. This modification would allow the inner ring to be stretched open wider by grasping the tab on each half; pulling apart the apparatus to further increase the inner hole or area (which surrounds the patient's digit); and relaxing the tension on the device, which allows the ring to return to its original size.

This embodiment would allow the user to increase the ring size as needed in order to pull over larger digits (thumbs, big toes) and also to increase the size of the central hole when removing the ring so that the T-Ring device does not contact the digit when removed.

This embodiment would further eliminate the need to snap the inner frame apparatus at the score points to remove the ring device, and would maintain the integrity of the ring device when the central hole needed to be enlarged. The T-Ring device could be stretched apart and then allowed to relax (as often as needed) to accomplish putting this surgical apparatus on and taking it off the patient's digit.

Potential Uses:

The "T-Ring" device has been developed to provide a bloodless operating field for emergent and non-emergent medical procedures. It is designed to temporarily restrict blood flow so that the treating health care professional may accomplish a procedure with maximum visibility in the field, which is usually only possible after obtaining adequate hemostasis of the area involved.

While the primary indication for the "T-Ring" device will be its use in procedures involving the fingers and thumbs, it also may be used with the same effect in procedures involving the digits of the lower extremities. The primary indications for use of the "T-Ring" device would be exploration and repair of acute finger and toe injuries and to provide a bloodless operating field in elective finger and toe procedures. The invention can be applied to many potential uses, including but not limited to: wound repair (soft tissue skin avulsion or laceration), wound exploration and repair (injuries of the hands/feet involving tendons, bones or joint), foreign body exploration and elective procedures of the fingers and toes.

This invention also is intended for temporary use in situations where a typical medical environment is not available such as in the wilderness or a military battlefield situation. With the addition of a plastic bag or wrapper to "T-Ring" apparatus, the user in the field, work place, or any non-medical facility can quickly treat a finger or toe wound until proper medical personnel can be reached. The "T-Ring" apparatus can be used in conjunction with plastic wrap or a plastic bag to help contain the wound and to keep the wound together. Further, the plastic bag or wrapper can also help to move the apparatus on and off the finger or toe.

This T-Ring device can be used for veterinary applications and for different size animal appendages. This embodiment would include larger and varied dimensions of the preferred embodiments described within this application.

Embodiments Shown in FIGS. 8 to 22:

FIGS. 8 to 22 show views of other preferred embodiments of the invention. The most basic version of the invention is a frame with a flexible membrane layer and an opening in said flexible membrane layer. FIGS. 8 to 22 show the non-pneumatic tourniquet device invention, which is designed for quick, easy application to the involved digit (finger or toe) or other appendage of the patient. There is an apparatus 10 for improving an operating field for medical procedures comprising a substantially rigid frame 15 with a flexible membrane 20, which lies within the circumference of the frame or mounted within the frame. This invention may also have application in the urological area for treatment of the male penis.

FIGS. 8 to 15 show embodiments with the frame having a first tab 60 and a second tab 65 at the opposite ends of the frame body. Other embodiments may allow for more than two tabs, which are strategically located around the frame body to further assist the physician or user in removing or utilizing the T-Ring apparatus. In the embodiments shown, the inner surface of the frame is relatively smooth; however, in other embodiments, this inner surface can have grooves or breaks in the surface, which can help anchor the elastic membrane layer to the inner surface of the frame.

Figure 8:
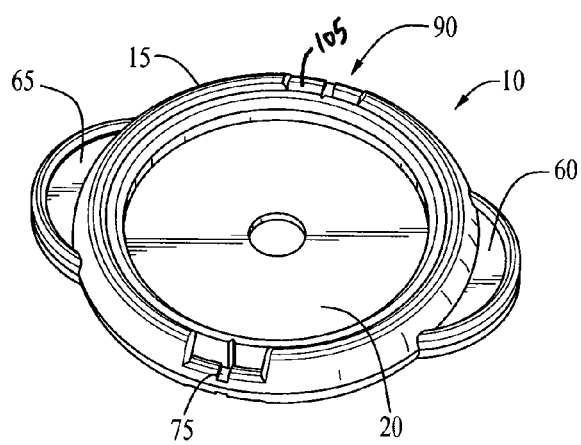
FIG. 8 is a perspective view of another preferred embodiment of the invention, which shows the flexible membrane layer disposed within the frame.
Figure 9:
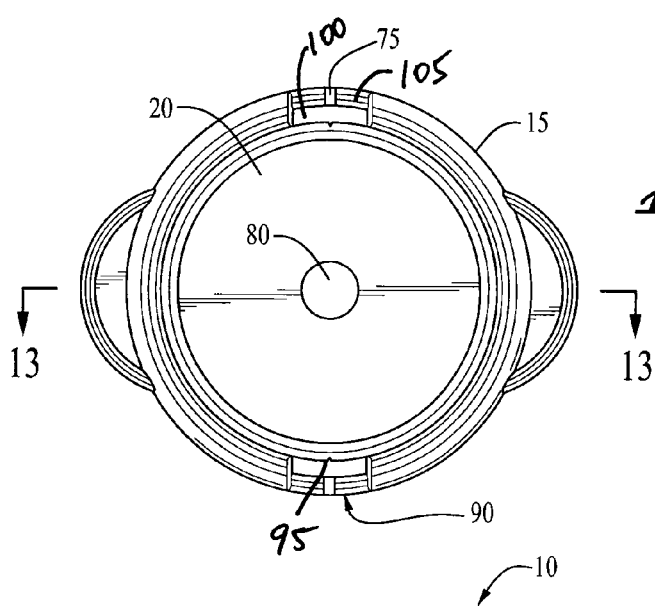
FIG. 9 is a view of a first side or top of the preferred embodiment shown in FIG. 8; the second side view or bottom is a mirror image of the first side view.
Figure 10:
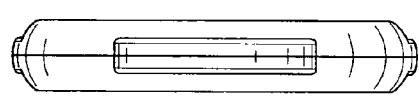
FIG. 10 is a view of a third side of the preferred embodiment shown in FIG. 8.
Figure 11:
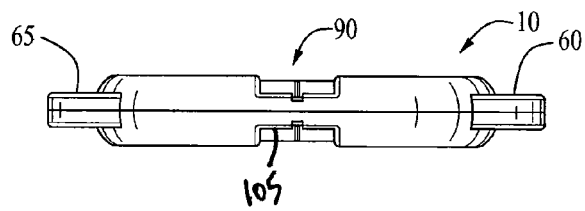
FIG. 11 is a view of a fifth side of the preferred embodiment shown in FIG. 8.

The frame can also have at least one break point area 90, scoring, groove 75 or indentation, which is oriented in between the first and the second end. FIGS. 8 to 9 show two break points 90 or score areas, which are located between the first and the second end; each break point is oppositely opposed to one another. This break point or breakable area 90 allows the user to more easily snap the frame (from a first unsnapped position to a second snapped position) so that the user can expand the apparatus further beyond the non-snapped frame diameter, especially over any repaired area of the patient's finger or digit or other appendage (arm or leg).

In FIGS. 8 to 9, these break points or score areas are of a larger area than the score 75 or groove area of the embodiment shown in FIG. 6. These break points can allow the continuity of the frame, but the amount of frame material in this "break point" area will be less, which in turn would lead to different heights and depths of this "break point" area from the surrounding parts of the frame. The dimensions of the "break point areas" can be varied.

Figure 12:
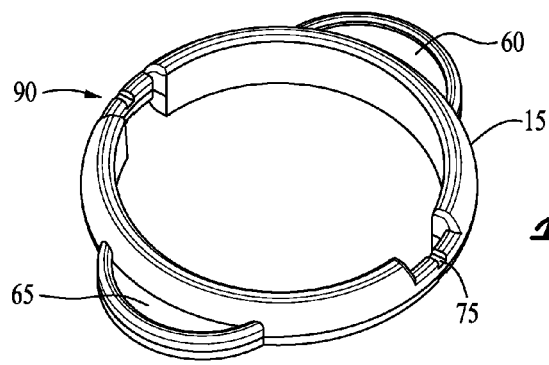
FIG. 12 is a perspective view of the frame of the preferred embodiment shown in FIG. 8 and without the flexible membrane.
Figure 13:
FIG. 13 is a cross-sectional view of the invention as shown in FIG. 8.
Figure 14:
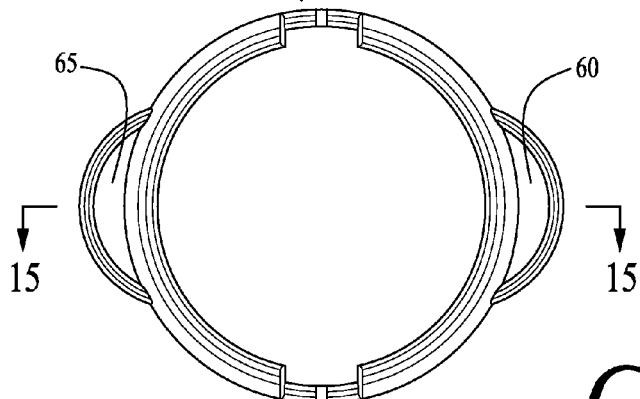
FIG. 14 is a view of a first side or top of the frame of FIG. 12; the second side view or bottom is a mirror image of the first side view.
Figure 15:
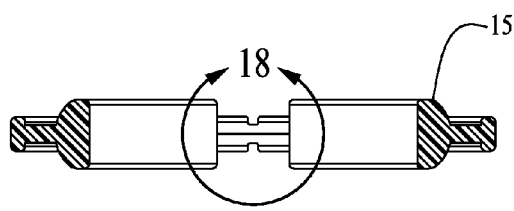
FIG. 15 is a cross-sectional view of the frame of FIG. 12 and along the sight lines shown in FIG. 14.
Figure 16:
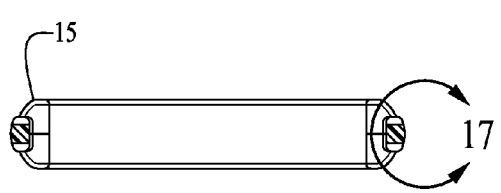
FIG. 16 is a cross-sectional view of the frame of FIG. 12 and along the sight lines shown in FIG. 14.

In FIGS. 12 to 14, the frame has at least one and preferably two "break point areas." The "break point area" has a bridge area that connects the two sides of the frame. The top surface of the bridge area is at lower elevation than the top of the frame. The inner surface of the bridge area is at greater distance from the center of the T-Ring apparatus than the inner surface of the frame (when measured along the same line from the center of the apparatus). This "bridge area" forms a shelf structure in the frame.

In addition, in FIGS. 8 and 12, there is a second or smaller score point or break point in the central area of the bridge, which further helps the user break the frame, when needed (during removal of the T-Ring apparatus).

In addition, the break point areas can be further defined in comparison to the frame. The frame has a first cross-section thickness, and the break point area has a second cross-section thickness; the first cross-section thickness is greater than the second cross-section thickness. In other words, the break point or breakable area has a smaller cross-sectional area than the rest of the frame.

In FIGS. 8 and 9, this break point area can also be described as a shelf or cleft or recess 105. Looking from the top and bottom surfaces of the apparatus, the shelf 105 can be formed into the body of the frame; there can be multiple shelf, clefts or recesses at one break point area or on opposite sides of the apparatus. This shelf can share a common uniform exterior perimeter with the rest of the rigid frame (minus any external tabs or grips). The shelf or bridge area can have a smaller or thinner thickness than the rest of the frame but will still be continuous with the rest of the frame.

In FIGS. 8 and 9, a flexible layer or membrane 20 engages the frame (within or around or partially around) and substantially covers the frame opening. This flexible layer or membrane has a membrane opening 80, which is centrally located in the device. The material used for the flexible membrane can be thermoplastic elastomer (TPE) or other types of rubbers, plastics or flexible materials. This flexible layer can lie partially or completely within the frame. This flexible layer or membrane acts similar to the embodiments disclosed above.

The size of the membrane opening 80 should be large enough to accommodate the patient's digit or body part and to provide resistance in order to effectively provide pressure to the digit as the apparatus is slid into place or for effective exsanguination of the body part or digit.

Test data has shown that this invention is superior over other devices (such as the Tournicot or a rolled up latex glove finger) in providing an ideal amount of pressure for effective exsanguination of the finger or appendage. This invention is equally useful for different sized appendages or fingers or toes.

As noted above, the process to manufacture the preferred embodiment is to injection mold a single frame piece (including without limitation a hard plastic outer ring or frame piece such as polycarbonate or polypropylene). Then, or at the same time as the formation of the frame, the single frame piece can "over-molded" with the flexible material (including without limitation thermoplastic elastomer or TPE). During this injection molding process, these two different materials (hard plastic frame and the elastic membrane layer) are bonded by heat during manufacturing.

In another embodiment wherein the flexible membrane lies within the frame, there is a two step manufacturing: 1. First Shot—hard outer ring is formed; then 2. Second Shot—the inner flexible membrane portion is formed within seconds of the First Shot so that the two materials are still hot and can bind to one another.

Other embodiments allow for multiple frame pieces, but for cost savings, it is preferable to injection mold a single frame piece and co-mold the TPE layer at the same time to take advantage of the heat of the process to form a suitable bond between the frame material and the TPE layer.

A most basic version of this invention can also employ a flexible but at the same time firm plastic or rubber-style ring or frame piece. The central rubber disc is made with a "hole" in its center, which allows the "T-Ring" apparatus to be placed over a finger or toe. This hole or opening is smaller than the diameter of the involved digit, so that pressure will be applied to the digit as the ring is slid into place. Other embodiments envision the outer ring to be a single piece unit that houses or contains or holds the center rubber disc.

In other embodiments, the frame has a shelf or flange that runs substantially around the inner surface of the frame, with the exception of the break point areas. The flexible membrane engages this inner surface flange. Note how the peripheral edge of the flexible membrane is substantially thicker or at a greater thickness than the rest of the flexible membrane layer (see FIG. 21). In one particular embodiment, the inner surface of the frame, with the exception of the break point areas, is relatively smooth. The flexible membrane engages this inner frame surface.

At its peripheral edge, flexible membrane layer is at a lower elevation than the top surface of the frame. The break point areas have bridge areas and scoring points. In FIGS. 19 to 20, the flexible membrane layer's peripheral edge can have at least one groove or slit 95, which corresponds to the score point on the frame. The groove or slit is designed to be a lead point where, once the outer ring is snapped, the user can tear the inner membrane to remove the T-Ring apparatus from the patient's digit or appendage. The tear can be started at this groove or slit. In other embodiments, the flexible membrane layer can partially cover the frame.

As shown in FIG. 9, there is at least one channel or opening 100 formed by the bridge or shelf piece 105 within the breakable portion 90 and the flexible membrane. This channel 100 can run through the apparatus.

To use the device: the health care provider will grip the "T-Ring" device or apparatus by its outer hardened ring or frame and slide the apparatus up the finger or toe to its base on the hand or foot. The outer ring "drags" the inner section or membrane with it, effectively exsanguinating the digit as the "T-Ring" apparatus is placed on the digit.

Since the membrane is flexible and is secured to the frame and lags behind it during application, the inner hole is effectively pulled up and over any protrusions on the digit. This central flexible disc structure or membrane further allows the "T-Ring" device to slide over lacerations, avulsions and, more importantly, traumatic skin flaps. Once in place, the "T-Ring" device or apparatus applies enough pressure to maintain hemostasis, and thus, this invention provides a bloodless operating field.

As with the embodiment above, at the break points and score points, the frame can be snapped or broken, and the central hole may be enlarged by pulling on the opposing halves of the outer ring. This will allow the "T-Ring" device to be removed from the digit without the flexible membrane material from the central disc coming into contact with the repaired portion of the digit; this structure allows for a safe and efficient removal. This invention allows for the ring apparatus to be easily removed from the finger in the same fashion that it was placed on the finger; this "snap" option provides an additional margin of safety with more complex injuries or procedures.

The "T-Ring" device allows for differing sizes or diameters of the central rubber hole or opening. There is a standard sized hole or opening, which will be utilized on the majority of patients. There will also be versions of the invention with smaller central holes or openings in the cases that increased pressure is necessary to achieve hemostasis, and rings with larger holes in the case where there may be an unusually large flap or irregularity that must be accommodated by the "T-Ring". This invention capitalizes on the difference in flexibility and resistance between the outer ring and the inner flexible ring. In the embodiments shown in FIG. 8 to 22, other embodiments can employ other features and structures as listed above.

Other Embodiments of the Invention (Split Version):

In this "split ring version," the frame has a first frame part and a second frame part. An inner flexible ring connects the first and the second frame parts. The inner flexible ring can have opposite ends with notches and grooves, which are cut or "scored" at the terminal edge of the ring. The inner flexible ring has an opening for engaging the finger, toe or appendage of the patient.

In another embodiment of the invention (Pediatric-Toe Version), the outer frame is rectangular shaped or having two sides with a shorter length than the other two sides of the device. This narrow shape better allows use on toes of a child; the space between the toes and fingers of a child are typically less than of an adult. The frame can have break points or score areas, which better enable the user to break the frame, when the apparatus is to be removed from the patient.

An apparatus for improving an operating field for medical procedures for a patient comprising: a frame with a peripheral edge and a first end and a second end; the frame further having a centrally disposed frame opening and at least one break point area, which is oriented in between the first end and the second end; the frame having a first cross-section thickness, and the at least one break point area having a second cross-section thickness; the first cross-section thickness being greater than the second cross-section thickness; a flexible membrane is disposed within the frame and substantially covers the frame opening; the flexible membrane having a centrally disposed membrane opening; the flexible membrane and the at least one break point area form at least one channel through the apparatus and at the peripheral edge of the frame; the first end of the frame has a first tab; the second end of the frame has a second tab; and the first and the second tabs outwardly extend past the peripheral edge of the frame; whereby the apparatus can engage an appendage of the patient with said flexible membrane to provide an effective exsanguination of said appendage (an arm, a leg or a digit). The at least one break point area can further have a groove.

An apparatus for improving an operating field for medical procedures for a patient comprising: a frame with a peripheral edge and a first end and a second end; the frame further having a first centrally disposed opening and at least one breakable portion, which is oriented in between the first end and the second end; the frame having a first thickness; the at least one breakable portion having a second thickness; the first thickness of the frame being greater than the second thickness of the at least one breakable portion; the frame and the at least one breakable portion can share a common external perimeter or boundary, so that the outer circumference of the apparatus remains uniformly the same (minus any tab or grip extensions).

A flexible membrane can be fixedly connected within the frame and substantially covers the first centrally disposed opening; and the membrane having a second centrally disposed opening; whereby the apparatus can engage an appendage of the patient with said flexible membrane and through the second centrally disposed opening to provide an effective exsanguination of said appendage; the at least one breakable portion further has a groove; the first end and the second ends of the frame can have tabs or gripping surfaces; and the first and the second tabs outwardly extend past the peripheral edge of the frame; the flexible membrane and the at least one breakable portion can form at least one channel through the apparatus and at the peripheral edge of the frame.

An apparatus for a patient comprising: a rigid frame with a peripheral edge and a first end and a second end; the rigid frame further having a first centrally disposed opening and at least one breakable portion; the at least one breakable portion defining a shelf or a ridge or cleft; said shelf being continuous with said rigid frame; a flexible membrane is disposed within the rigid frame and substantially covers the first centrally disposed opening; the flexible membrane having a second centrally disposed opening; the at least one breakable portion and the flexible membrane forming a third opening near the peripheral edge of the rigid frame and through the apparatus; whereby the apparatus can engage an appendage of the patient with said flexible membrane to provide an effective exsanguination of said appendage, and whereby the at least one breakable portion can be snapped to allow the apparatus to be stretched away and removed from the patient; the flexible member further comprises at least one notch; and said shelf can have a groove.

While the invention as described above in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

Further, any underlined section headings are not intended to be limiting in relation to the interpretation of patent claim coverage. The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention. Any heading or section titles are for simple organization for the reader and are not intended to be limiting as to claim scope, construction or interpretation.

We claim:

1. An apparatus for improving an operating field for medical procedures for a patient comprising:
   a frame with a peripheral edge and a first end and a second end;
      the frame further having a centrally disposed frame opening and at least one break point area, which is oriented in between the first end and the second end;
      the frame having a first cross-section thickness, and the at least one break point area having a second cross-section thickness; the first cross-section thickness being greater than the second cross-section thickness;
      a flexible membrane is disposed within the frame and substantially covers the frame opening; the frame having a non-snapped frame diameter;
      the flexible membrane having a centrally disposed membrane opening;
      the flexible membrane and the at least one break point area form at least one channel through the apparatus and at the peripheral edge of the frame;
      the first end of the frame has a first tab;
      the second end of the frame has a second tab; and
      the first and the second tabs outwardly extend past the peripheral edge of the frame;
      whereby the apparatus can engage an appendage of the patient with said flexible membrane to provide an effective exsanguination of said appendage;
   the at least one break point allows a user to snap the frame from a first unsnapped position to a second snapped position, so that the user can expand the apparatus further beyond the non-snapped frame diameter and apply or remove over any injured or repaired area of the patient's appendage; and in the second snapped position, the flexible membrane remains unbroken throughout an entire circumference of the apparatus.

2. The apparatus of claim 1, wherein the appendage is an arm, a leg or a digit.

3. The apparatus of claim 1, wherein the at least one break point area further having a groove.

4. An apparatus for improving an operating field for medical procedures for a patient comprising:
   a frame with a peripheral edge and a first end and a second end;
   the frame further having a first centrally disposed opening and at least one breakable portion, which is oriented in between the first end and the second end;
   the frame having a first thickness;
   the at least one breakable portion having a second thickness;
   the first thickness of the frame being greater than the second thickness of the at least one breakable portion;
   the frame and the at least one breakable portion share a common external perimeter;
   a flexible membrane is fixedly connected within the frame and substantially covers the first centrally disposed opening; and the membrane having a second centrally disposed opening;
   the frame having a non-snapped frame diameter;
   whereby the apparatus can engage an appendage of the patient with said flexible membrane and through the second centrally disposed opening to provide an effective exsanguination of said appendage;
   the at least one breakable portion allows a user to snap the frame from a first unsnapped position to a second snapped position, so that the user can expand the apparatus further beyond the non-snapped frame diameter and apply or remove over any injured or repaired area of the patient's appendage; and in the second snapped position, the flexible membrane remains unbroken throughout an entire circumference of the apparatus.

5. The apparatus of claim 4, wherein the at least one breakable portion further has a groove.

6. The apparatus of claim 4, wherein the first end of the frame has a first tab; the second end of the frame has a second tab; and the first and the second tabs outwardly extend past the peripheral edge of the frame.

7. The apparatus of claim 4, wherein the appendage is an arm, a leg or a digit.

8. The apparatus of claim 4, wherein the flexible membrane and the at least one breakable portion form at least one channel through the apparatus and at the peripheral edge of the frame.

9. An apparatus for a patient comprising:
   a rigid frame with a peripheral edge and a first end and a second end;
   the rigid frame further having a first centrally disposed opening and at least one breakable portion;
   the at least one breakable portion defining a shelf;
   said shelf being continuous with said rigid frame;
   a flexible membrane is disposed within the rigid frame and substantially covers the first centrally disposed opening;
   the flexible membrane having a second centrally disposed opening;
   the at least one breakable portion and the flexible membrane forming a third opening near the peripheral edge of the rigid frame and through the apparatus;
   the frame having a non-snapped frame diameter;
   whereby the apparatus can engage an appendage of the patient with said flexible membrane to provide an effective exsanguination of said appendage, and whereby the at least one breakable portion can be snapped to allow the apparatus to be stretched away and removed from the patient;
   the at least one breakable portion allows a user to snap the frame from a first unsnapped position to a second snapped position, so that the user can expand the apparatus further beyond the non-snapped frame diameter and apply or remove over any injured or repaired area of the patient's appendage; and in the second snapped position, the flexible membrane remains unbroken throughout an entire circumference of the apparatus.

10. The apparatus of claim 9, wherein the flexible member further comprises at least one notch.

11. The apparatus of claim 9, wherein the first end of the rigid frame has a first tab; the second end of the rigid frame has a second tab; and the first and the second tabs outwardly extend past the peripheral edge of the rigid frame.

12. The apparatus of claim 9, wherein said shelf having a groove.

* * * * *